United States Patent
Imamura et al.

(10) Patent No.: US 7,160,422 B2
(45) Date of Patent: Jan. 9, 2007

(54) GAS SENSOR INCORPORATING A MULTILAYERED GAS SENSING ELEMENT

(75) Inventors: Shinichiro Imamura, Chiryu (JP); Susumu Naito, Kariya (JP); Makoto Nakae, Nagoya (JP); Namitsugu Fujii, Yokkaichi (JP)

(73) Assignee: Denso Corporation (JP)

( * ) Notice: Subject to any disclaimer, the term of this patent is extended or adjusted under 35 U.S.C. 154(b) by 693 days.

(21) Appl. No.: 10/404,122

(22) Filed: Apr. 2, 2003

(65) Prior Publication Data

US 2003/0188969 A1    Oct. 9, 2003

(30) Foreign Application Priority Data

Apr. 3, 2002 (JP) ............................. 2002-101541
Jan. 31, 2003 (JP) ............................. 2003-023419

(51) Int. Cl.
*G01N 27/407* (2006.01)

(52) U.S. Cl. ..................... 204/431; 204/424

(58) Field of Classification Search ............... 204/424, 204/431

See application file for complete search history.

(56) References Cited

U.S. PATENT DOCUMENTS 5,288,389 A    2/1994 Yamada et al.
5,419,828 A    5/1995 Nakano et al.
5,830,339 A  * 11/1998 Watanabe et al. ............ 204/426
2003/0146093 A1 *  8/2003 Akiyama et al. ............ 204/424

FOREIGN PATENT DOCUMENTS

JP    7-120429    5/1995
JP    2659793    6/1997

* cited by examiner

*Primary Examiner*—Nam Nguyen
*Assistant Examiner*—Anthony Fick
(74) *Attorney, Agent, or Firm*—Nixon & Vanderhye PC

(57) ABSTRACT

A multilayered gas sensing element 2 is positioned in a cylindrical housing 10 via a cylindrical insulator 3. The multilayered gas sensing element 2 includes a narrow-width portion 21 and a wide-width portion 22. The wide-width portion 22 is in a fixed relationship with respect to the insulator 3. The narrow-width portion 21 is in a floating relationship with respect to the insulator 3. The narrow-width portion 21 has a gas sensing portion for detecting the concentration of a specific gas contained in a measuring objective gas.

4 Claims, 13 Drawing Sheets

COMPARATIVE EXAMPLE

COMPARATIVE EXAMPLE

GAS SENSOR INCORPORATING A MULTILAYERED GAS SENSING ELEMENT

BACKGROUND OF THE INVENTION

1. Field of the Invention

The present invention relates to a gas sensor usable for combustion control of an internal combustion engine for an automotive vehicle.

2. Description of the Background Art

A gas sensor is generally installed in an exhaust system of an automotive engine to use a sensing signal for combustion control. For example, as disclosed in U.S. Pat. No. 5,288,389, this kind of gas sensor includes a multilayered gas sensing element made of ceramic members for detecting the concentration of a specific gas contained in the exhaust gas.

In general, the multilayered gas sensing element includes a predetermined number of thin ceramic substrates stacked or laminated on one another. The ceramic substrates are weak in mechanical strength and therefore may be broken when subjected to vibrations or shocks.

Especially, the weakest portion of the gas sensor is a protruding end portion of the multilayered gas sensing element protruding from a front or distal end of the insulator.

Shortening the protruding length of the multilayered gas sensing element is effective to eliminate such damage. However, the protruding end portion of the multilayered gas sensing element is a portion where a sensing portion is provided to detect the gas concentration. The gas concentration sensing portion needs to be exposed to a measuring objective gas in a measuring objective gas side cover. To assure accurate detection of the gas concentration, it is necessary to maintain the temperature of the gas concentration sensing portion. This is why the heater is integrally provided with the gas sensing element, or separately provided, to heat the gas sensing element.

If the protruding length of the multilayered gas sensing element is shortened, the heat to be used for warming up the gas sensing element will leak via the insulator and the housing. In other words, it will be difficult to maintain the temperature of the gas concentration sensing portion to a constant value, as it is located in the protruding portion of the gas sensing element. To avoid this, a minimum protruding length must be secured. Hence, the protruding length of the gas sensing element cannot be shortened so much.

Nowadays, the multilayered gas sensing elements used in the automotive engines or the like are required to have excellent warm-up or activation properties. In general, this kind of multilayered gas sensing elements cannot operate normally to detect the gas concentration unless the temperature reaches the activation level. When the combustion control mechanism must start its operation immediately after the automotive engine starts up, it is definitely necessary to accurately detect the gas concentration as quickly as possible. To this end, the multilayered gas sensing element is heated by a heater to promptly increase the temperature of the element to the activation level.

To realize such immediate or prompt activation of the gas sensing element, reducing the size of the multilayered gas sensing element is effective in that the heat capacity decreases.

However, incorporating a compact multilayered gas sensing element into a gas sensor will encounter with the following restrictions.

Referring not to an example of the present invention (FIG. 1) which will be later explained, this type of gas sensor 1 includes a multilayered gas sensing element 2 fixed to a housing 10.

The multilayered gas sensing element 2 includes electric terminals (265 and 266 as shown in FIG. 2) for supplying electric power to this element 2 and for outputting a sensing signal from this element 2. Plate terminals 131 are electrically brought into contact with these terminals (refer to FIG. 1).

To assure insulation between plate terminals 131, the multilayered gas sensing element 2 needs to be inserted into an insulator 3 and securely fixed to this insulator 3. Then, the assembly of the multilayered gas sensing element 2 and the insulator 3 needs to be inserted into the housing 10 and securely fixed to this housing 10.

In this case, a seal member 30 is provided to fix the multilayered gas sensing element 2 and the insulator 3. To secure the strength of the seal member 30, the width of the multilayered gas sensing element 2 cannot be reduced so much. In general, the required number of the plate terminals 131 is four, i.e., two at the front side and two at the rear side according to the illustration of FIG. 2. To assure the insulation between these plate terminals 131, the width of the multilayered gas sensing element 2 cannot be reduced so much. On the other hand, there are no specific restrictions regarding the downsizing of the gas sensing portion.

SUMMARY OF THE INVENTION

In view of the foregoing problems of the prior art, the present invention has an object to provide a gas sensor equipped with a multilayered gas sensing element possessing sufficient durability against shocks.

In order to accomplish the above and other related objects of the present invention, the present invention provides a gas sensor including a cylindrical housing, and a multilayered gas sensing element positioned at a predetermined position in the housing via a cylindrical insulator. The multilayered gas sensing element includes a narrow-width portion and a wide-width portion. A width of the narrow-width portion is shorter than a width of the wide-width portion. The wide-width portion is in a fixed relationship with respect to the insulator. The narrow-width portion is in a floating relationship with respect to the insulator. And, the narrow-width portion has a gas sensing portion for detecting the concentration of a specific gas contained in a measuring objective gas.

BRIEF DESCRIPTION OF THE DRAWINGS

The above and other objects, features, aspects and advantages of the present invention will become more apparent from the following detailed description of the present invention which is to be read in conjunction with the accompanying drawings, in which.

DESCRIPTION OF THE PREFERRED EMBODIMENTS

Figure 1:
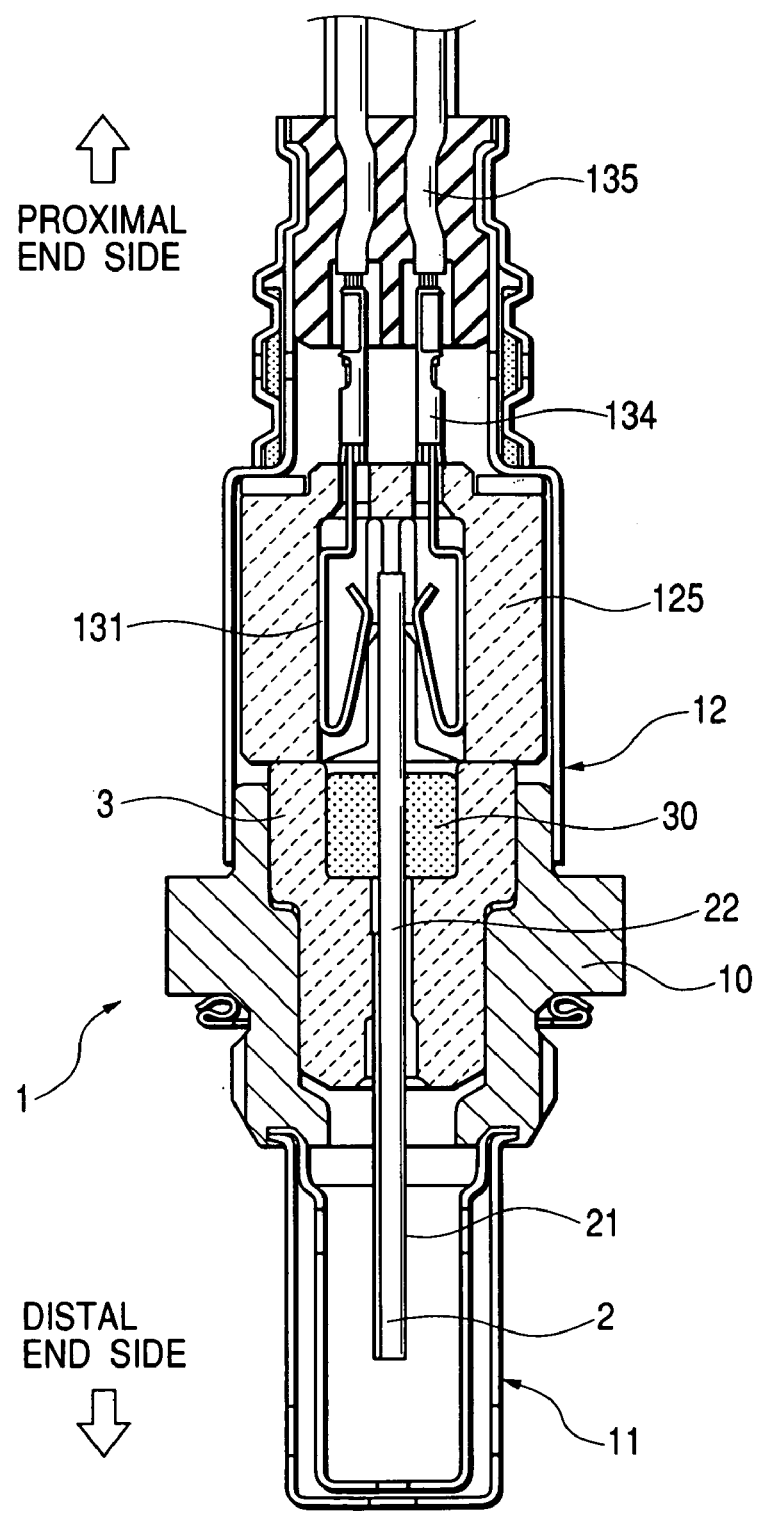
FIG. 1 is a vertical cross-sectional view showing a gas sensor in accordance with a first embodiment of the present invention.

The present invention provides a gas sensor including a cylindrical housing, and a multilayered gas sensing element positioned at a predetermined position in the housing via a cylindrical insulator. The multilayered gas sensing element includes a narrow-width portion and a wide-width portion. A width of the narrow-width portion is shorter than a width of the wide-width portion. The wide-width portion is in a fixed relationship with respect to the insulator. The narrow-width portion is in a floating relationship with respect to the insulator. And, the narrow-width portion has a gas sensing portion for detecting the concentration of a specific gas contained in a measuring objective gas.

The multilayered gas sensing element of this invention includes the narrow-width portion and the wide-width portion. The wide-width portion is in a fixed relationship with respect to the insulator. The narrow-width portion is in a floating relationship with respect to the insulator.

According to the gas sensor of this invention, holding or fixing of the multilayered gas sensing element to the insulator is performed by disposing the wide-width portion at a proximal end side of the gas sensor and disposing the narrow-width portion at a distal end side of the gas sensor. Then, only the wide-width portion is fixed to the inside surface of the insulator by using an adhesive or sealing agent, or by using a fastening member.

When any shock or vibration is applied on the gas sensor, the narrow-width portion swings or oscillates as it is supported in a cantilever fashion (i.e., in a floating relationship) with respect to the wide-width portion. In other words, a significant amount of moment acts to the narrow-width portion of the multilayered gas sensing element.

If the width of the floating portion is substantially the same as that of the fixed portion, the above moment may break the floating portion.

The present invention can reduce the probability of the floating portion being broken, because the width of the floating portion is reduced compared with that of the fixed portion. Reducing the width of the floating portion is effective to reduce the weight of the floating portion. The moment acting on the floating portion becomes small. The durability can be improved.

Furthermore, the narrow-width portion is small in both of volume and heat capacity compared with the wide-width portion. Thus, forming the narrow-width portion according to the present invention is advantageous in realizing the immediate or prompt activation of the multilayered gas sensing element.

From the foregoing, the present invention can provide a gas sensor equipped with a multilayered gas sensing element possessing sufficient durability against shocks.

According to a preferable embodiment of the gas sensor of the present invention, the multilayered gas sensing element incorporates an electrochemical cell consisting of an oxygen ion conductive solid electrolytic substrate, a measuring objective gas side electrode provided on the solid electrolytic substrate, and a reference electrode provided on the solid electrolytic substrate. The multilayered gas sensing element measures the concentration of a specific gas contained in the measuring objective gas based on the oxygen ion current flowing across the electrochemical cell.

Furthermore, the multilayered gas sensing element is constituted by an adequate number of stacked or laminated substrates including the above solid electrolytic substrate and insulating or other substrates.

For example, the multilayered gas sensing element of the present invention is an oxygen sensing element which is capable of measuring the concentration of oxygen contained in the measuring objective gas.

Furthermore, the multilayered gas sensing element of the present invention is usable as another type of gas sensing element which decomposes a specific gas, such as NOx, CO and HC, to produce oxygen ions and measures the concentration of the specific gas based on the oxygen ions.

Furthermore, the multilayered gas sensing element of the present invention is installable in the exhaust gas system of an internal combustion engine to measure the oxygen concentration in the exhaust gas. The measured oxygen concentration is usable to detect or estimate the air-fuel (A/F) ratio of gas mixture introduced into a combustion chamber of the engine.

In any case, the role of the gas sensor is changeable depending on the type of the element.

Later-described embodiments of the present invention show practical arrangements of the gas sensor in accordance with the present invention. However, the effects of the present invention will be obtained even in any other type of gas sensor when the multilayered gas sensing element has the narrow-width portion and the wide-width portion.

Furthermore, the multilayered gas sensing element of the present invention is an elongated plate element having a rectangular cross-sectional area when taken along a plane normal to the longitudinal axis of the element. In this case, the width of the element is defined by the length of the element measured along the direction normal to the longitudinal direction of the element and also normal to the thickness direction (refer to w1 and w2 shown in FIG. 4).

When the boundary between the wide-width portion and the narrow-width portion is configured into a right angle, a concentrated stress may act at this corner when the multilayered gas sensing element is subjected to vibrations and shocks. This may lead to generation of cracks or breakage. To avoid this, it is preferable to form a curved or tapered surface at the boundary between the wide-width portion and the narrow-width. For example, the curved surface is equivalent to a circle of 0.3 mm to 1.0 mm in radius.

Furthermore, when the multilayered gas sensing element is fixed to the gas sensor at the wide-width portion, it is desirable that the entire surface of the wide-width portion is brought into contact with the inner surface of the insulator. Alternatively, it is possible to fix the wide-width portion to the insulator at one or more local portions.

Furthermore, the gas sensing portion of the present invention is a portion which greatly contributes to the measurement of a specific gas concentration in the measuring objective gas. For example, according to a later-described embodiment shown in FIG. 8, the portion corresponding to the electrodes constituting a censor cell serves as the gas sensing portion of the present invention.

Furthermore, it is preferable that a thickness of the narrow-width portion is larger than a thickness of the wide-width portion.

With this arrangement, it becomes possible to increase the strength of the narrow-width portion and accordingly improve the durability against shocks.

Figure 5:
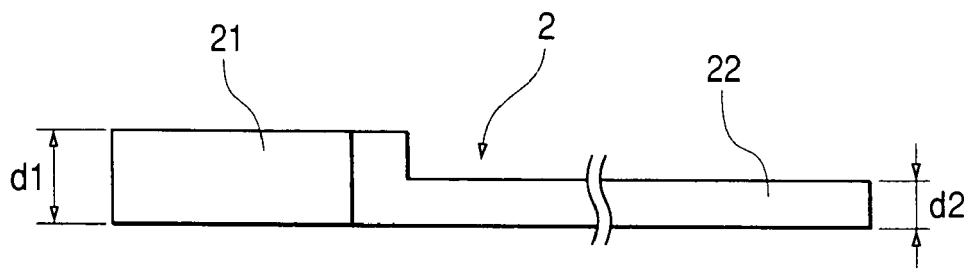
FIG. 5 is a side view showing the multilayered gas sensing element in accordance with the first embodiment of the present invention.

In this case, the thicknesses of the narrow-width and the wide-width portion are defined by the length measured along the line parallel to the lamination of the layers constituting the multilayered gas sensing element (refer to d1 and d2 shown in FIG. 5).

Figure 6:
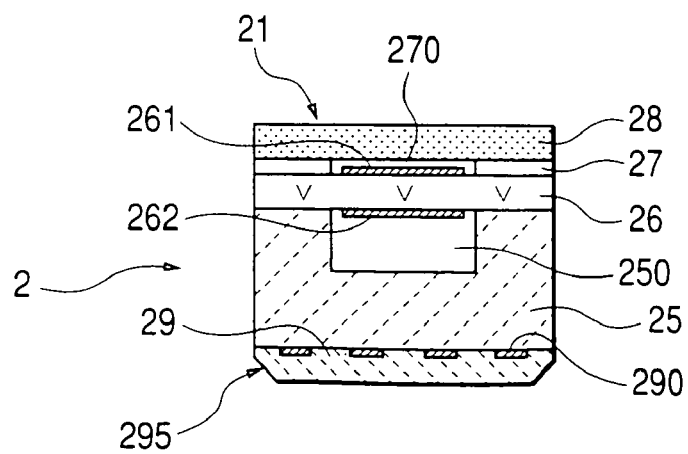
FIG. 6 is a cross-sectional view explaining the multilayered gas sensing element in accordance with the first embodiment of the present invention.
Figure 12:
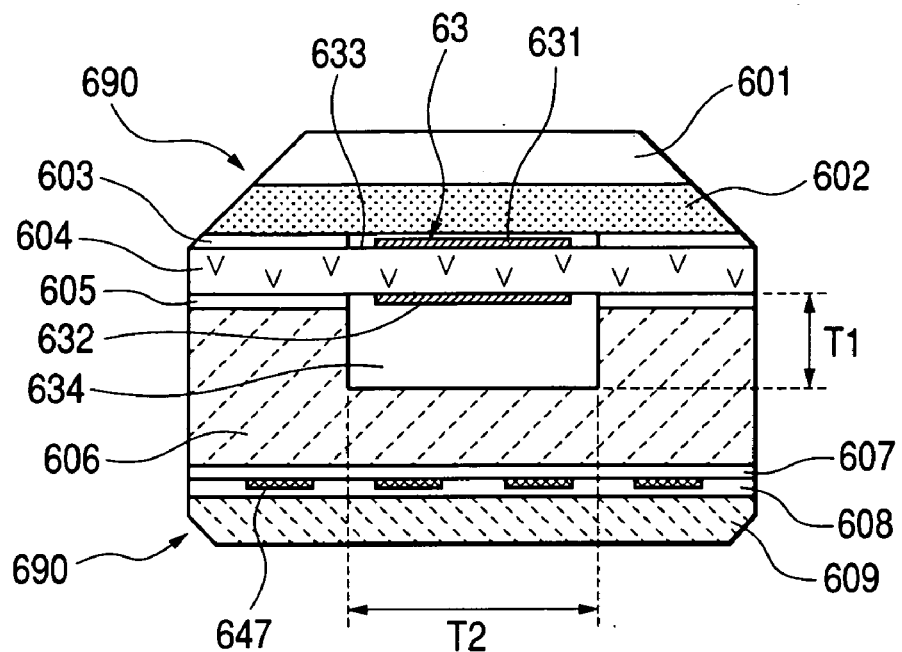
FIG. 12 is a cross-sectional view showing the multilayered gas sensing element in accordance with the third embodiment of the present invention, taken along a line A—A of FIG. 10.

Furthermore, it is preferable that the multilayered gas sensing element has a corner portion being configured into a tapered or curved surface (refer to FIGS. 6 and 12).

Every corner of the multilayered gas sensing element tends to be subjected to a concentrated stress. Hence, forming the tapered or curved surface is effective to relax or moderate such a concentrated stress. Accordingly, it becomes possible to provide a multilayered gas sensing element possessing satisfactory durability against shocks.

Furthermore, it is preferable that the thickness of the wide-width portion is in the range from 0.7 mm to 2.0 mm, and the width of the wide-width portion is in the range from 4.0 mm to 6.0 mm. The thickness of the narrow-width portion is in the range from 1.3 mm to 2.4 mm, and the width of the narrow-width portion is in the range from 2.5 mm to 4.0 mm. And, the narrow-width portion has the length equal to or larger than 8.0 mm.

The above-described dimensions of the multilayered gas sensing element assures sufficient durability against cracks or breakage which may occur in the process of installing the multilayered gas sensing element into the gas sensor. In the event that the electric terminals are provided for outputting the gas concentration sensing signal and for supplying electric power, it is easy to secure insulation space between these terminals. In addition, this arrangement not only assures the immediate or prompt activation but also brings excellent mechanical strength.

Regarding the thickness of the above-described wide-width portion, it is preferable that the thickness is not smaller than 0.7 mm to assure sufficient strength of the wide-width portion for preventing the multilayered gas sensing element from being cracked or broken when assembled with various constituent members of the gas sensor. Meanwhile, to assure insulation between the above-described electric terminals, it is desirable that the width of the wide-width portion is not smaller than 4.0 mm.

However, the heat capacity of the multilayered gas sensing element increases with increasing thickness and width. Having excessively large heat capacity is disadvantageous in realizing the immediate or prompt activation of the multilayered gas sensing element. In view of this, it is desirable that the thickness of the above-described wide-width portion is not larger than 2.0 mm and the width of the wide-width portion is not larger than 6.0 mm.

Furthermore, there is the possibility that the narrow-width portion becomes thicker because of the presence of the gas sensing portion. As described above, excessively increasing the thickness is disadvantageous in realizing the immediate or prompt activation of the multilayered gas sensing element. Hence, it is desirable that the thickness of the narrow-width portion is not larger than 2.4 mm. On the other hand, considering the durability of the multilayered gas sensing element necessary when assembled with various constituent members of the gas sensor, it is preferable that the thickness of the narrow-width portion is not smaller than 1.3 mm.

Regarding the width of the narrow-width portion, from the reason that the sufficient durability is required when the multilayered gas sensing element is assembled with various constituent members of the gas sensor, it is preferable that the width of the narrow-width portion is not larger than 4.0 mm.

Although reducing the size of the multilayered gas sensing element is advantageous in realizing the immediate or prompt activation of the multilayered gas sensing element, an excessively small area cannot efficiently receives the heat supplied from the heater. From this, it is desirable that the width of the narrow-width portion is not smaller than 2.5 mm.

Furthermore, if the length of the narrow-width portion is excessively short, the heat will easily leak to the insulator or the like. Hence, to maintain the narrow-width portion including the gas sensing portion at a constant temperature, it is preferable that the length of the narrow-width portion is not smaller than 8.0 mm.

Furthermore, excessively elongating the narrow-width portion is undesirable because a large moment will act on the narrow-width portion supported in a floating relationship with respect to the insulator when it is subjected to the above-described vibrations and shocks. Therefore, it is desirable that the length of the narrow-width portion is not larger than 20.0 mm.

Furthermore, it is desirable that the multilayered gas sensing element includes a sensor cell and a heater. The sensor cell includes a solid electrolytic substrate, a first electrode provided on the solid electrolytic substrate so as to be exposed to the measuring objective gas, and a second electrode provided on the solid electrolytic substrate so as to be exposed to a reference gas. The heater includes a heat generating element for generating heat in response to electric power supply so as to increase the temperature of the sensor cell up to the activation level. And, a minimum distance between the heat generating element of the heater and a closest one of the first and second electrodes of the sensor cell is in the range from 0.4 mm to 1.8 mm.

From the view point that sufficient strength is necessary during the installation of the multilayered gas sensing element, excessively shortening the clearance between the heat generating element and the electrode is undesirable in that it may trigger the cracks. The minimum distance not shorter than 0.4 mm is required. On the other hand, thickening the multilayered gas sensing element is disadvantageous in that the immediate or prompt activation of the multilayered gas sensing element cannot be realized. It is therefore desirable that the thickness is not larger than 1.8 mm. With the above-described dimensions, it becomes possible to obtain the multilayered gas sensing element possessing which is satisfactory in strength and excellent in activation properties.

Figure 13:
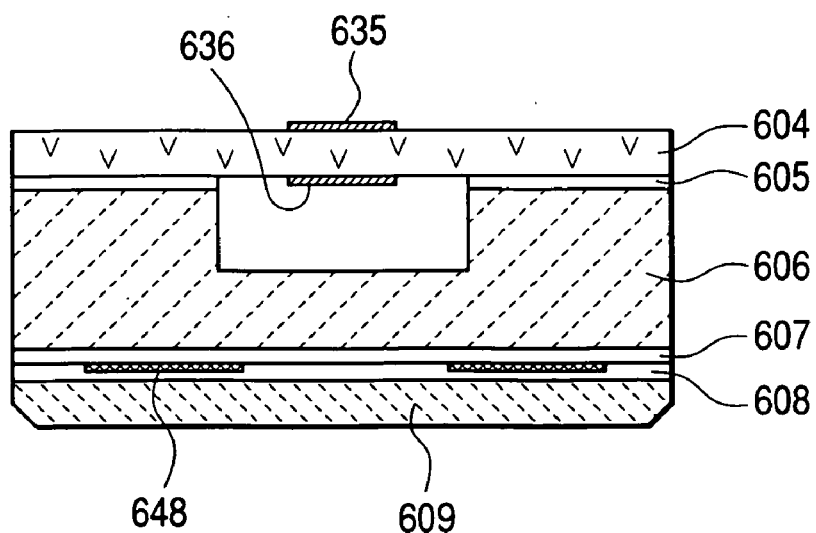
FIG. 13 is a cross-sectional view showing the multilayered gas sensing element in accordance with the third embodiment of the present invention, taken along a line B—B of FIG. 10.

For example, the minimum distance is substantially equal to the thickness of a spacer located between the heat generating element and the electrode (refer to FIG. 13).

First Embodiment

FIGS. 1 through 6 show a gas sensor 1 of the first embodiment of the present invention. The gas sensor 1 has a cylindrical housing 10, and a multilayered gas sensing element 2 positioned at a predetermined position in the housing 10 via a cylindrical insulator 3. The multilayered gas sensing element 2 consists of a narrow-width portion 21 and a wide-width portion 22 having a width larger than that of the narrow-width portion 21. The wide-width portion 22 is in a fixed relationship with respect to the insulator 3. The narrow-width portion 21 is in a floating relationship with respect to the insulator 3. The narrow-width portion 21 has a gas sensing portion for detecting the concentration of a specific gas contained in a measuring objective gas.

As shown in FIG. 1, the gas sensor 1 of the first embodiment has an atmospheric air side cover 12 attached to a proximal end side of the cylindrical housing 10. A measuring objective gas side cover 11 is attached to a distal end side of the cylindrical housing 10. The multilayered gas sensing element 2 is placed in the insulator 3 which is positioned in the housing 10.

An atmospheric air side insulator 125 is provided at the proximal end side of the insulator 3.

A proximal end side of the multilayered gas sensing element 2 is located in the atmospheric air side insulator 125. Electric terminals 265 and 266 (refer to FIG. 2), provided at the proximal end side of the multilayered gas sensing element 2, are connected to the leads 135 via a plurality of plate terminals 131 and joint members 134.

Furthermore, a distal end side of the multilayered gas sensing element 2 is exposed in the measuring objective gas side cover 11 to measure a specific gas concentration in the measuring objective gas.

Figure 2:
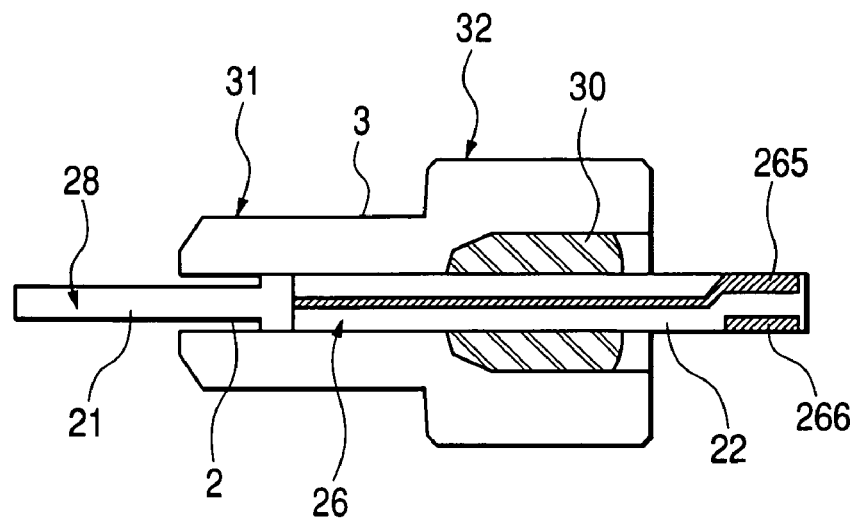
FIG. 2 is a cross-sectional view explaining a multilayered gas sensing element in fixed to an insulator in accordance with the first embodiment of the present invention.
Figure 3:
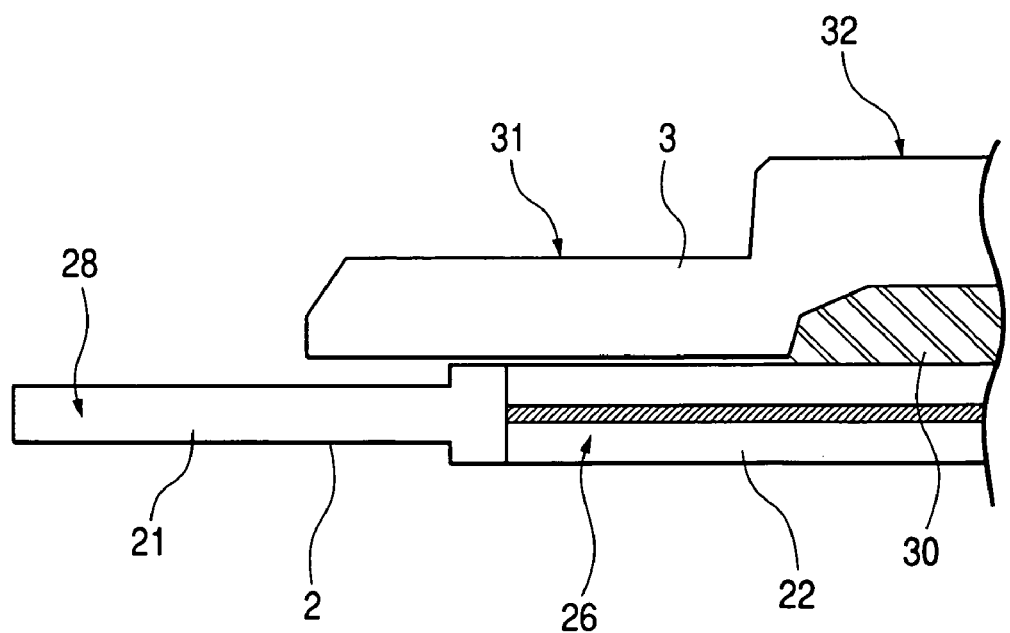
FIG. 3 is an enlarged cross-sectional view explaining an essential part of the fixation between the multilayered gas sensing element and the insulator in accordance with the first embodiment of the present invention.

The insulator 3, as shown in FIGS. 2 and 3, has a proximal end portion configured into a large-diameter portion 32 and a distal end portion configured into a small-diameter portion 31, which forms a cylindrical shape as a whole. The multilayered gas sensing element 2 is inserted into the insulator 3. A seal member 30 airtightly seals the clearance between the outer surface of the multilayered gas sensing element 2 and the inner surface of the insulator 3. The seal member 30 is a fixing member for securely fixing the multilayered gas sensing element 2 in a predetermined position relative to the insulator 3.

The seal member 30 is, for example, made of glass materials, talc or other powder seal materials, or various heat resistive adhesive resins.

The portion where the multilayered gas sensing element 2 is fixed by the seal member 30 is limited to the wide-width portion 22. As shown in FIGS. 2 and 3, the clearance between the large-diameter portion 32 of the insulator 3 and the wide-width portion 22 of the multilayered gas sensing element 2 is fully staffed with the seal member 30. The wide-width portion 22 is firmly fixed to the insulator 3. However, no seal member 30 is provided between the narrow-width portion 21 and the insulator 3. The wide-width portion 22 is supported in a cantilever fashion. Namely, the wide-width portion 22 is in a floating relationship with respect to the insulator 3.

Hereinafter, the multilayered gas sensing element 2 will be explained in more detail.

Figure 4:
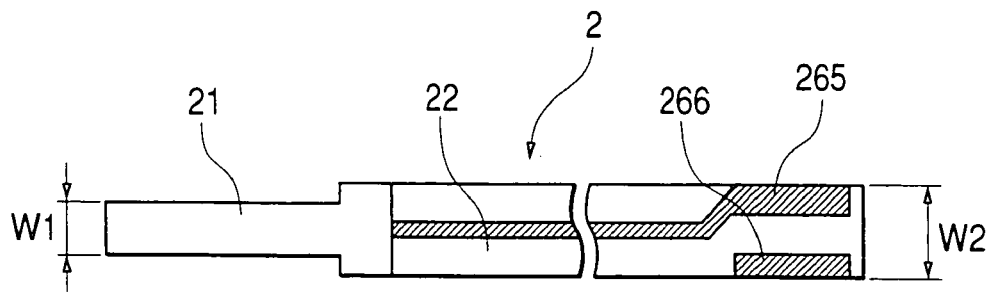
FIG. 4 is a plan view showing the multilayered gas sensing element in accordance with the first embodiment of the present invention.

As shown in FIGS. 4 to 6, the multilayered gas sensing element 2 includes an oxygen ion conductive solid electrolytic substrate 26 which is configured into a flattened and elongated rectangular body. A pair of electrodes 261 and 262 is provided on the opposed surfaces of the solid electrolytic substrate 26. The lower electrode 262 is exposed to a reference gas chamber 250 defined in a spacer 25. The upper electrode 261 is exposed to a measuring objective gas chamber 270 constituted by a spacer 27 and a diffusion resistive layer 28. A heater substrate 29, equipped with a heat generating element 290 when electric power is supplied, is attached or laminated on the lower surface of the spacer 25.

The multilayered gas sensing element 2, as shown in FIG. 4, includes a distal end portion provided with the electrodes 261 and 262 and configured into the narrow-width portion 21 and a proximal end portion provided with the terminals 265 and 266 and configured into the wide-width portion 22. In other words, the gas sensing portion 21 (constituted by the electrodes 261 and 262) is located in the narrow-width portion 21. The width w1 of the narrow-width portion 21 is uniform. The width w2 of the wide-width portion 22 is uniform, too. The terminals 265 and 266 are used for outputting the sensing signal of the multilayered gas sensing element 2.

Furthermore, as shown in FIG. 5, the thickness d1 of the narrow-width portion 21 is larger than the thickness d2 of the wide-width portion 22. The thickness d1 of the narrow-width portion 21 is uniform. The thickness d2 of the wide-width portion 22 is uniform, too. The cross-sectional area of the multilayered gas sensing element 2 is rectangular. As shown in FIG. 6, tapered portions 295 are formed at both corners of the heater substrate 29. Providing the tapered portions 295 effectively prevents the concentrated tress from acting on the corners of the heater substrate 29, thereby improving the durability of the multilayered gas sensing element 2 against shocks. FIG. 6 is the cross-sectional view taken at the narrow-width portion 21.

The gas sensor in accordance with the first embodiment has the following functions and brings the following effects.

According to the gas sensor 1 of this embodiment, the holding or fixing of the multilayered gas sensing element 2 to the insulator 3 is performed by disposing the wide-width portion 22 at the proximal end side of the gas sensor 1 and disposing the narrow-width portion 21 at the distal end side of the gas sensor 1, and then fixing only the wide-width portion 22 to the inside surface of the insulator 3 by using the seal member 30.

The weak portion where the cracks and breakage tend to appear when subjected to shocks is the floating portion of the multilayered gas sensing element 2 which is not directly fixed to the insulator 3. Considering this fact, the first embodiment of the present invention reduces the width of the floating portion of the multilayered gas sensing element 2 compared with the fixed portion of the multilayered gas sensing element 2. Reducing the width of the floating portion of the multilayered gas sensing element 2 makes it possible to effectively prevent the concentrated stress from acting on the floating portion.

As described above, the first embodiment provides the gas sensor incorporating the multilayered gas sensing element possessing sufficient strength against shocks.

Second Embodiment

Figure 7:
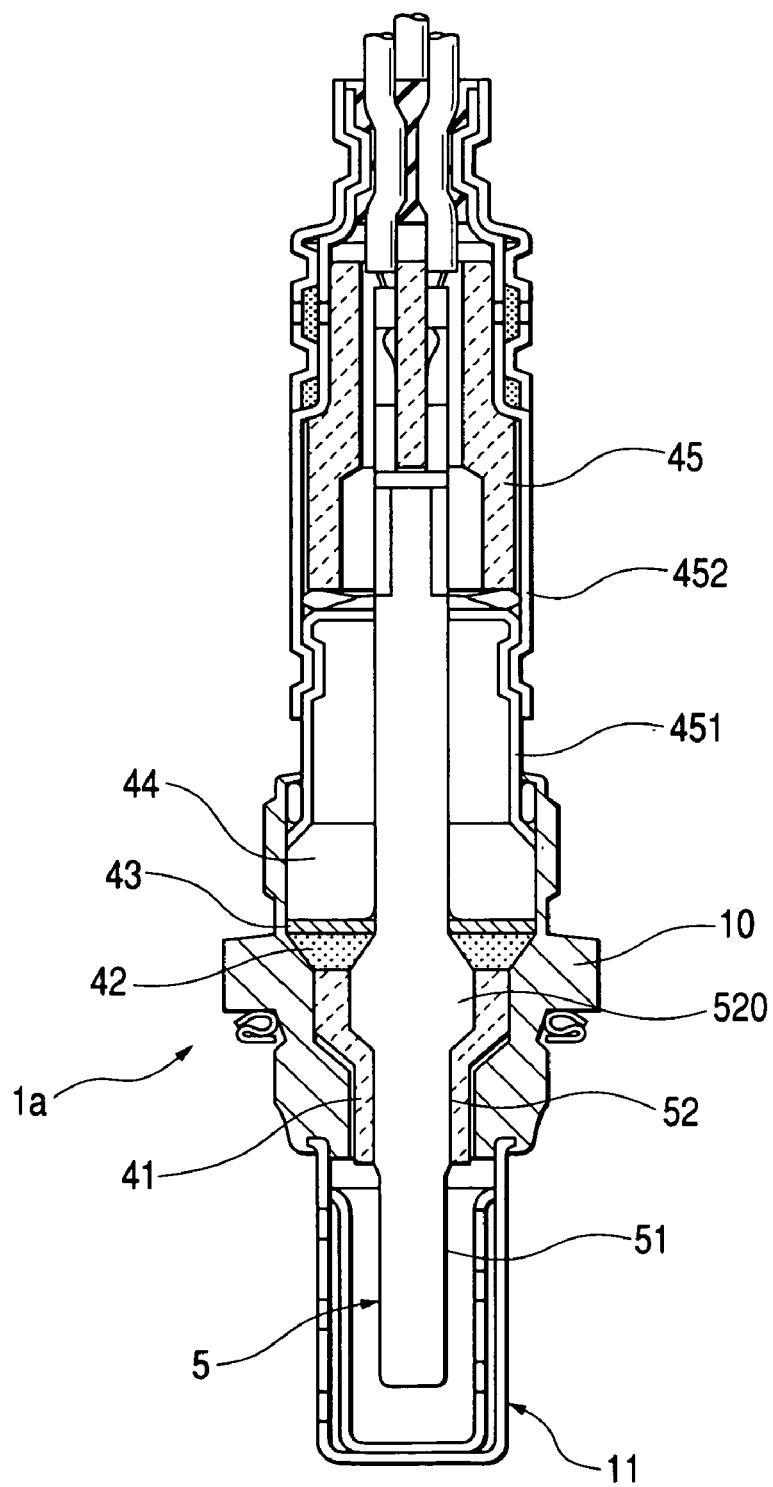
FIG. 7 is a vertical cross-sectional view explaining a gas sensor in accordance with a second embodiment of the present invention.

A gas sensor 1a of the second embodiment, as shown in FIG. 7, includes the housing 10, with a multilayered gas sensing element 5 disposed in the housing 10 via an insulator 41, a powder seal member 42, a packing 43, and an insulator 44.

Furthermore, the gas sensor 1a of this embodiment includes atmospheric air side covers 451 and 452 fixed by caulking to the upper side of the insulator 44 at the proximal end side of the housing 10. An atmospheric air side insulator 45 is disposed inside the atmospheric air side cover 452. Furthermore, the gas sensor 1a includes a measured gas side cover 11 attached to the distal end side of the housing 10.

The multilayered gas sensing element S of this embodiment has a narrow-width portion 51 and a wide-width portion 52, with a flange portion 520 formed at an upper (i.e., proximal) side of the wide-width portion 52. The flange portion 520 protrudes in the radial direction of the multilayered gas sensing element 5. The front (i.e., distal) end side of the flange portion 520 is received by (i.e., is brought into contact with) the housing 10.

Figure 8:
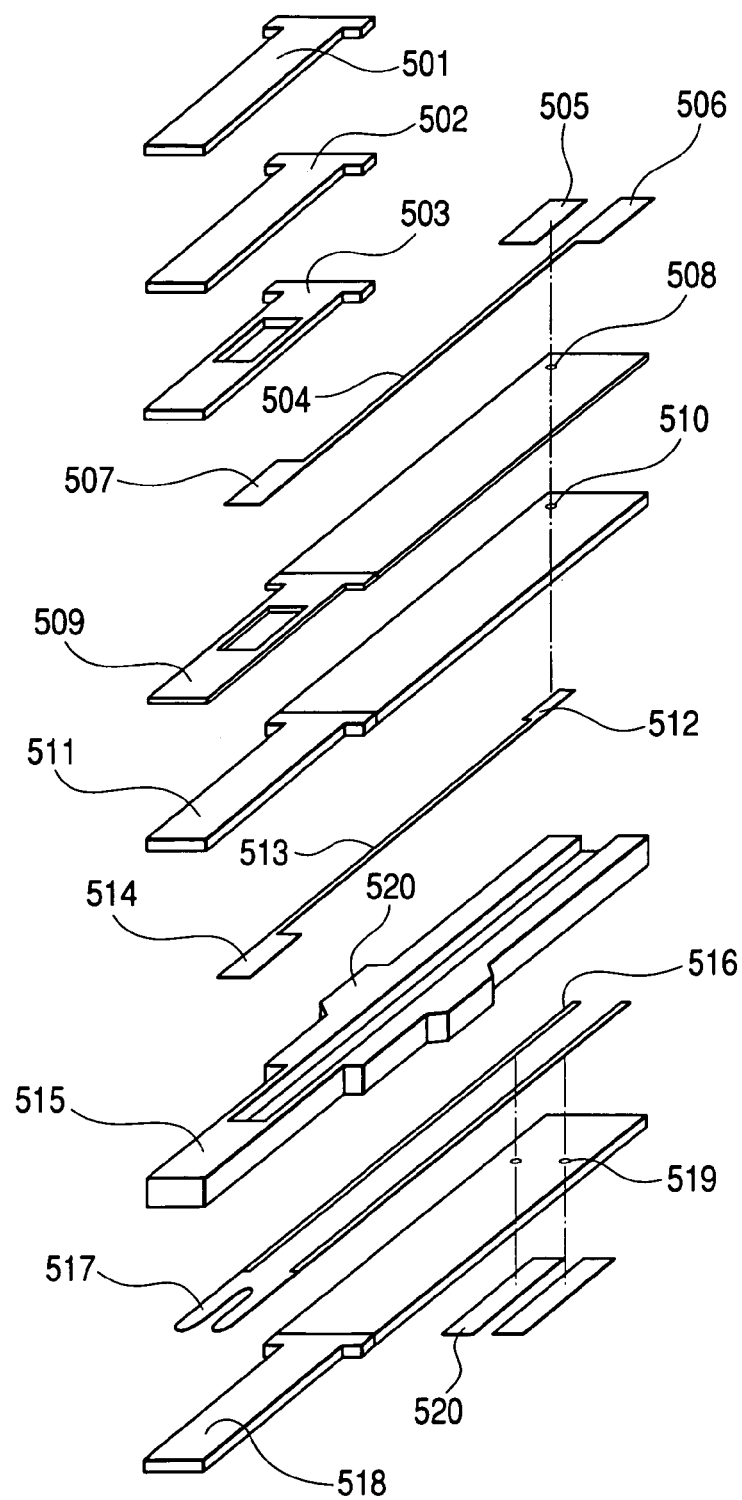
FIG. 8 is a perspective exploded view showing the multilayered gas sensing element in accordance with the second embodiment of the present invention.
Figure 9:
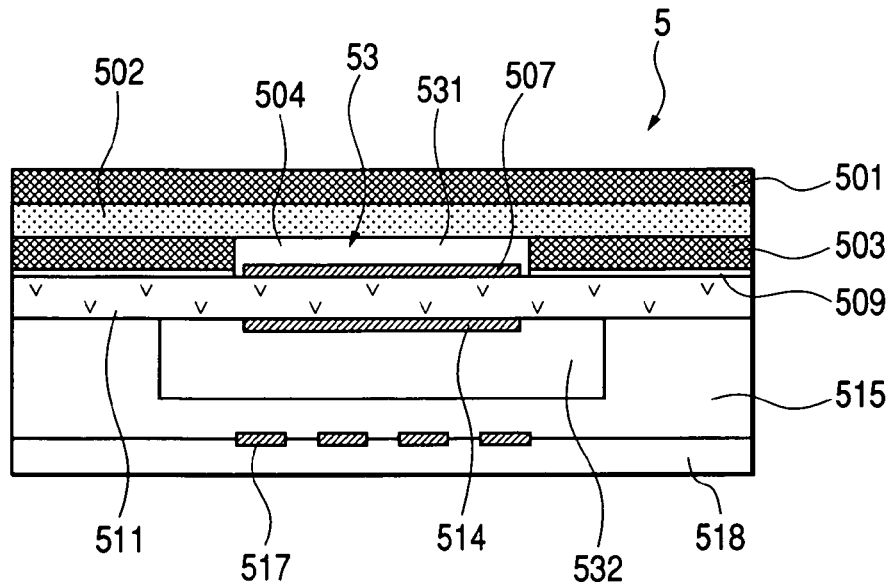
FIG. 9 is a cross-sectional view explaining the multilayered gas sensing element in accordance with the second embodiment of the present invention.

The multilayered gas sensing element 5 of this embodiment includes a gas shielding layer 501, a porous diffusion resistive layer 502, a spacer 503 defining a measuring objective gas chamber 531 therein, an insulating layer 509, a solid electrolytic substrate 511 forming a censor cell 53, a spacer 515 defining a reference gas chamber 532 therein, and a heater substrate 518 which are stacked or laminated in this order as shown in FIGS. 8 and 9. The solid electrolytic substrate 511 is made of zirconia ceramic. Other gas shielding layer 501 and the spacer 503 are made of alumina ceramic.

The sensor cell 53 includes an electrode 507 which is provided on the upper surface of the solid electrolytic substrate 511 so as to be exposed to the measuring objective gas chamber 531 and another electrode 514 which is provided on the opposite surface of the solid electrolytic substrate 511 so as to be exposed to the reference gas chamber 532. A lead portion 504 and a terminal portion 506, electrically connected to the electrode 507, are provided on the upper surface of the insulating layer 509. A lead portion 513 and an intermediate terminal portion 512, electrically connected to the electrode 514, are provided on the lower surface of the insulating layer 511. A through hole 508 and a though hole 510 continuously extends perpendicularly across the insulating layer 509 and the solid electrolytic substrate 511, respectively, so as to connect the intermediate terminal portion 512 to another terminal portion 505 provided on the upper surface of the insulating layer 509. The heater substrate 518 is provided with a heat generating element 517, lead portions 516, two through holes 519 and terminal portions 520.

The above-described gas sensing element 5 is manufactured in the following manner.

First, a required number of green sheets for the gas shielding layer 501, the porous diffusion resistive layer 502, the spacer 503, the solid electrolytic substrate 511, the spacer 515, and the heater substrate 518 are prepared according to the doctor blade method and the extrusion molding method. The spacer 515 is obtained through the steps of forming a groove in the green sheet and laminating the U-shaped sheet and a flat sheet.

Furthermore, the configuration of respective green sheets is substantially identical with that shown in FIG. 8 which is to be obtained through the sintering operation, although the green sheets shrink slightly during the sintering operation.

Next, an alumina paste is coated on the green sheet for the solid electrolytic substrate 511 to form a print region of the insulating layer 509. Then, a platinum paste is coated to form the print portions of the electrode 507, the electrode 514, the lead portions 504 and 513, and the terminal portions 505, 506 and 512. Next, pinholes for the through holes 508 and 510 are opened across the insulating layer 509 and the solid electrolytic substrate 511, respectively. The pinholes are stuffed with the conductive material.

Furthermore, a tungsten or platinum paste is coated on the green sheet for the heater substrate 518 to form print regions of the heat generating element 517, the lead portions 516, and the terminal portions 520. Furthermore, pinholes for the through holes 519 are opened across the heater substrate 518. Each pinhole is stuffed with the conductive material.

Next, respective green sheets are stacked or laminated to form a multilayered structure as shown in FIGS. 8 and 9. Then, the multilayered assembly of the green sheets is sintered under a predetermined given pressure at the temperature of 1,500° C. to 1,600° C. Through this sintering operation, the above-described multilayered gas sensing element 5 is finally obtained.

Next, various methods for forming the wide-width portion 52 and the narrow-width portion 51 of the above-described multilayered gas sensing element 5 will be explained.

One is a method for forming these portions 51 and 52 before the multilayered assembly of the green sheets is sintered. More specifically, respective green sheets are punched or cut beforehand and then laminated together. Alternatively, it is possible to punch or cut the green sheets after they are laminated.

The other one is a method for forming these portions 51 and 52 after the multilayered assembly of the green sheets was sintered. According to this method, the narrow-width portion is formed by grinding.

Any one of the above-described methods can be used to obtain the multilayered gas sensing element 5.

Third Embodiment

A multilayered gas sensing element 6 in accordance with the third embodiment is characterized by a curved or rounded boundary between the wide-width portion and the narrow-width portion.

The multilayered gas sensing element 6 of the third embodiment includes a gas shielding layer 601, a porous diffusion resistive layer 602, a spacer 603 defining a measuring objective gas chamber 633 therein, a solid electrolytic substrate 604 forming a sensor cell 63, an insulating layer 605, a spacer 606 defining a reference gas chamber 634 therein, insulating layers 607 and 608, and a heater substrate 609 which are stacked or laminated in this order as shown in FIGS. 10 to 13. The solid electrolytic substrate 604 is made of zirconia ceramic. Other gas shielding layer 601 and the spacer 603 are made of alumina ceramic.

The sensor cell 63 includes an electrode 631 which is provided on the upper surface of the solid electrolytic substrate 604 so as to be exposed to the measuring objective gas chamber 633 and another electrode 632 which is provided on the opposite surface of the solid electrolytic substrate 604 so as to be exposed to the reference gas chamber 634. A lead portion 635 and a terminal portion 637 are provided so as to be electrically connected to the electrode 631. A lead portion 636 and a terminal portion 638 are provided so as to be electrically connected to the electrode 632. Furthermore, a heat generating element 647, a lead portion 648 and terminals (not shown) are provided on the insulating layer 608 and the heater substrate 609.

FIG. 12 is a cross-sectional view taken along a transverse plane at the portion corresponding to the censor cell 63. FIG. 13 is a cross-sectional view taken along a transverse plane at the portion corresponding to the lead portions 635 and 636.

Furthermore, corner portions 690 of the multilayered gas sensing element 6 are chamfered into slant or tapered surfaces.

Figure 10:
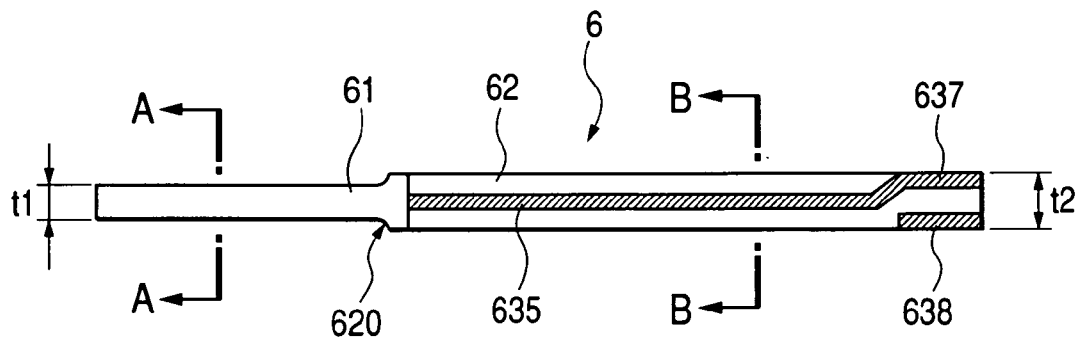
FIG. 10 is a plan view showing a multilayered gas sensing element in accordance with a third embodiment of the present invention.
Figure 11:
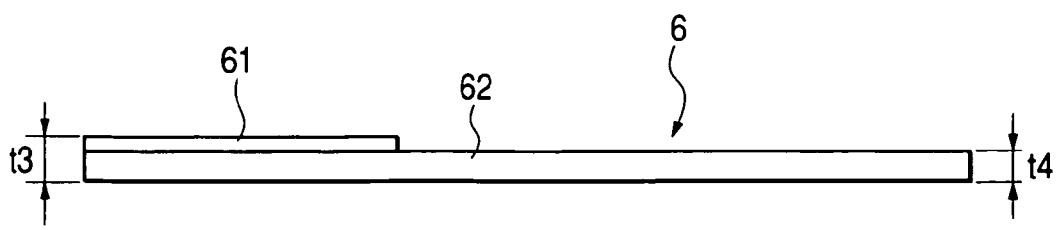
FIG. 11 is a side view showing the multilayered gas sensing element in accordance with the third embodiment of the present invention.

As shown in FIG. 10, according to the multilayered gas sensing element 6, a width t1 of narrow-width portion 61 is 3.2 mm. A width t2 of wide-width portion 62 is 4.5 mm. As shown in FIG. 11, a thickness t3 of narrow-width portion 61 is 2.1 mm. A thickness t4 of wide-width portion 62 is 1.6 mm.

Regarding the thickness of other constituent members of the multilayered gas sensing element 6, the gas shielding layer 601 is 0.16 mm, the porous diffusion resistive layer 602 is 0.24 mm, the spacer 603 is 0.03 mm, the solid electrolytic substrate 604 is 0.16 mm, the insulating layer 605 is 0.03 mm, the spacer 606 is 1.2 mm, the insulating layers 607 and 608 are both 0.03 mm, and the heater substrate 609 is 0.16 mm. A height T1 of the reference gas chamber 634 is 0.6 mm. A width T2 of the reference gas chamber 634 is 1.12 mm.

As shown in FIG. 10, according to the multilayered gas sensing element 6, a boundary 620 between the narrow-width portion 61 and the wide-width portion 62 is curved or rounded. The curvature of the boundary 620 is equivalent to a circle or arc having a diameter of 0.65 mm.

When the multilayered gas sensing element 6 is incorporated in a gas sensor, the multilayered gas sensing element 6 is fixed to the insulator at the wide-width portion 62. The narrow-width portion 61 is supported in a floating condition (i.e., in a cantilever fashion). The sensor cell 63 is formed within the narrow-width portion 61 so as to serve as the gas sensing portion.

The gas sensor incorporating the multilayered gas sensing element 6 functions in the same manner and brings the same effects as the first embodiment.

The minimum distance between the heat generating element 647 and the electrode 632 of the sensor cell 63 is a sum of the thicknesses of the spacer 606 and the insulating layer 607. According to this embodiment, the above minimum distance is 1.23 mm. To obtain a multilayered gas sensing element possessing sufficient strength and excellent activation properties, it is preferable that the above minimum distance is in the range from 0.4 mm to 1.8 mm.

The rest of this embodiment is substantially identical with that of the first embodiment.

Fourth Embodiment

Figure 14:
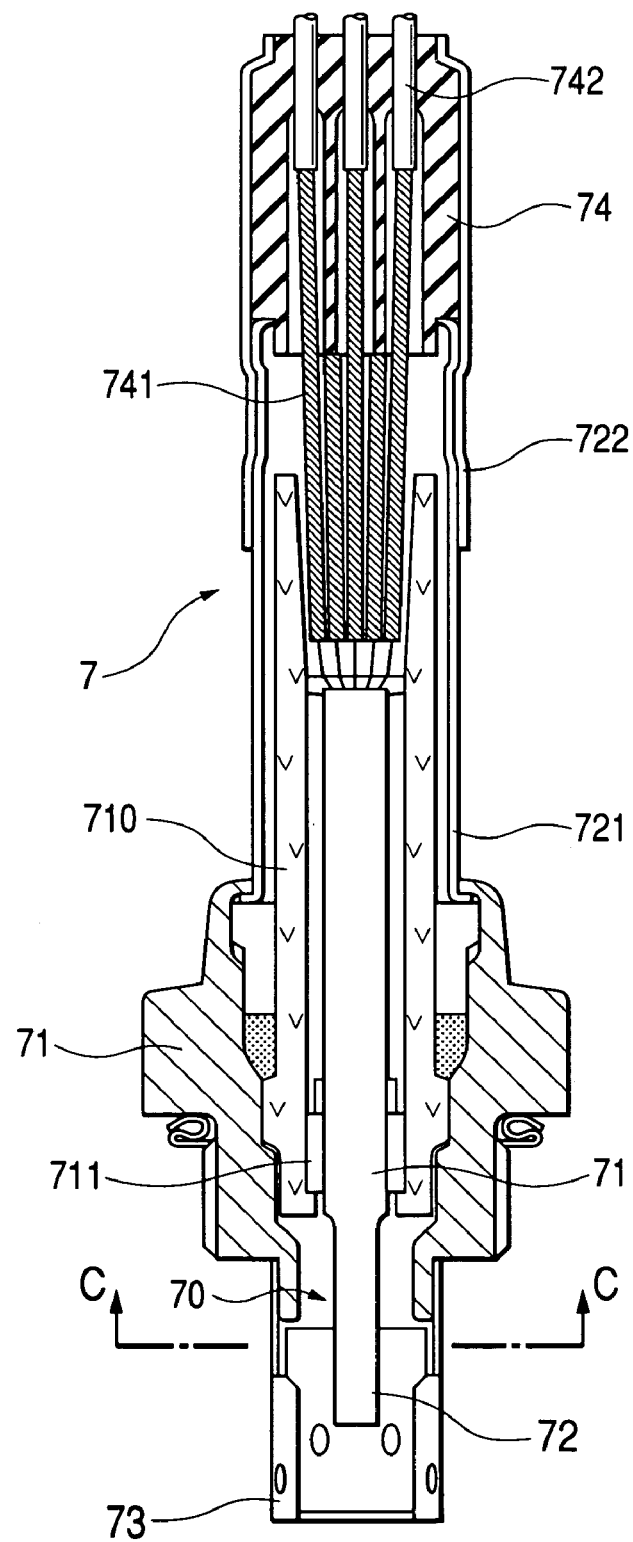
FIG. 14 is a vertical cross-sectional view explaining a gas sensor in accordance with a fourth embodiment of the present invention.
Figure 15:
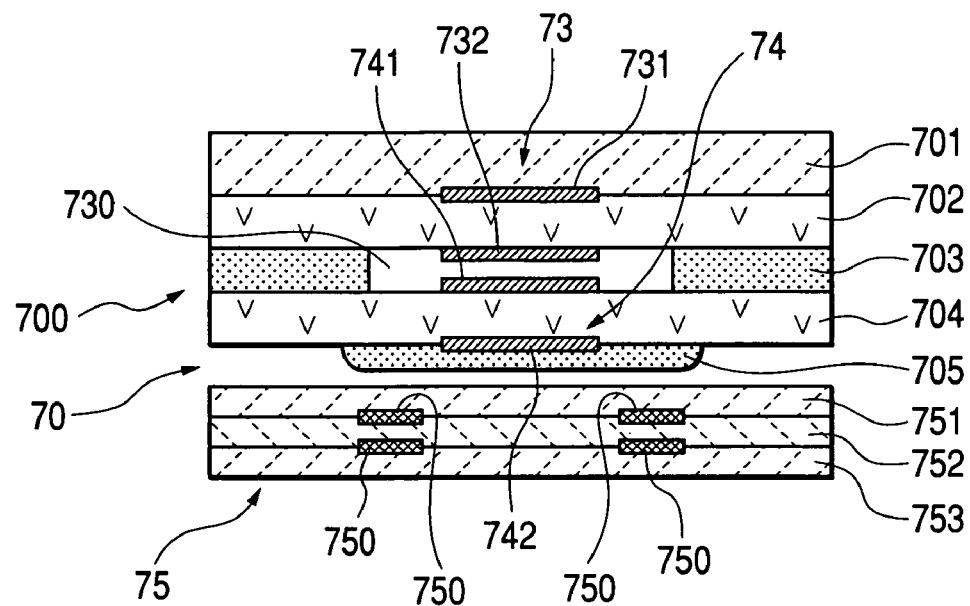
FIG. 15 is a cross-sectional view explaining a multilayered gas sensing element in accordance with the fourth embodiment of the present invention, taken along a line C—C of FIG. 14.

FIGS. 14 and 15 cooperatively show a gas sensor 7 of the fourth embodiment characterized in that a separate heater 75 is provided independent of a multilayered gas sensing element 70.

As shown in FIG. 14, the gas sensor 7 includes the multilayered gas sensing element 70 inserted and positioned in a housing 71, a measuring objective gas side cover 73 attached to a distal end side of the housing 71, and atmospheric air side covers 721 and 722 attached to a proximal end side of the housing. The members provided inside the atmospheric air side covers 721 and 722 are connectors 741 connected to the multilayered gas sensing element 70, leads 742 connected to the connectors 741 and extending out of the sensor body, an insulator 710 holding the multilayered gas sensing element 70 in the housing 71, and an elastic insulating member 74 having through holes for inserting the leads 742 and fixed by caulking to the proximal end of the atmospheric air cover 722.

The multilayered gas sensing element 70 includes a narrow-width portion 72 and a wide-width portion 71. The wide-width portion 71 is fixed to the inner surface of the insulator 710 via a ring member 711. The narrow-width portion 72 is supported in a floating condition (i.e., in a cantilever fashion).

Furthermore, the multilayered gas sensing element 70 includes a main body 700 consisting of a protecting layer 701, a solid electrolytic substrate 702, a porous layer 703, and a solid electrolytic substrate 704 stacked or laminated in this order as shown in FIG. 15. Furthermore, the multilayered gas sensing element 70 includes a separate heater 75 consisting of three insulating layers 751 to 753 and a heat generating element 750 embedded in these insulating layers 751 to 753.

The main body 700 includes a sensor cell 73 and a pump cell 74. Both the sensor cell 73 and the pump cell 74 are formed within the region of the narrow-width portion 72 so as to serve as the gas sensing portion.

The sensor cell 73 includes an electrode 731 formed on the upper surface of the solid electrolytic substrate 702 and covered by the dense and gas-impermeable protecting layer 701 and an electrode 732 provided on the lower surface of the solid electrolytic substrate 702 so as to be exposed to a measuring gas chamber 730 into which the measuring objective gas is introduced via the porous layer 703.

The pump cell 74 includes an electrode 741 provided on the upper surface of the solid electrolytic substrate 704 so as to be exposed to the measuring gas chamber 730 and an electrode 742 provided on the lower surface of the solid electrolytic substrate 704 covered by a porous protecting layer 705. The electrode 742 is opposed to the separate heater 75.

According to this embodiment, as shown in FIG. 14, the multilayered gas sensing element 70 is fixed to the insulator 710 at the lower portion (i.e., distal end side) of the wide-width portion 71. The upper part (i.e., the proximal end side) of the multilayered gas sensing element 70 is supported in a floating condition (i.e., in a cantilever fashion).

As apparent from the foregoing, the gas sensor 7 incorporating the multilayered gas sensing element 70 functions in the same manner and brings the same effects as the first embodiment. The rest of this embodiment is substantially identical with that of the first embodiment.

Fifth Embodiment

A multilayered gas sensing element 8 in accordance with the fifth embodiment of the present invention is a two-cell type element with a built-in heater.

Figure 16:
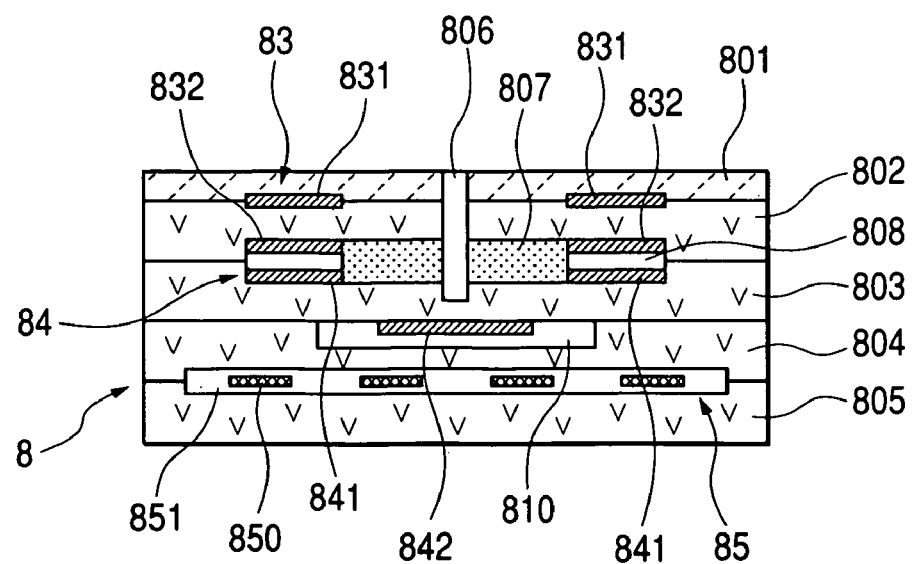
FIG. 16 is a cross-sectional view explaining a multilayered gas sensing element in accordance with a fifth embodiment of the present invention.

The multilayered gas sensing element 8 includes a protecting layer 801, solid electrolytic substrates 802 and 803, and additional substrates 804 and 805 stacked or laminated in this order as shown in FIG. 16. A measuring objective gas chamber 808, equipped with a porous layer 807, is defined between the solid electrolytic substrates 802 and 803. A gas introducing passage 806 extends across the protecting layer 801 and the solid electrolytic substrate 803 to introduce the measuring objective gas from the outside. The measuring objective gas enters into the measuring objective gas chamber 808 via the porous layer 807.

A heater 85, including a heat generating element 850 surrounded by an insulating layer 851, is embedded between two substrates 804 and 805.

The multilayered gas sensing element 8 includes a pump cell 83 and a sensor cell 84. The pump cell 83 includes an electrode 831 provided on the upper surface of solid electrolytic substrate 802 and covered by the protecting layer 801 and an electrode 832 provided on the lower surface of solid electrolytic substrate 802 so as to be exposed to the measuring objective gas chamber 808. The sensor cell 84 includes an electrode 841 provided on the upper surface of solid electrolytic substrate 803 so as to be exposed to the measuring objective gas chamber 808 and an electrode 842 provided on the lower surface of solid electrolytic substrate 803 so as to be exposed to a reference gas chamber 810. The reference gas chamber 810 is formed between the solid electrolytic substrates 803 and 804.

The multilayered gas sensing element 8 includes a wide-width portion and a narrow-width portion. The multilayered gas sensing element 8 is fixed to the insulator of the gas sensor at the wide-width portion. Both the pump cell 83 and the sensor cell 84 are provided within the region of the narrow-width portion so as to serve as the gas sensing portion. Thus, the multilayered gas sensing element 8 of this embodiment functions in the same manner and brings the same effects as the first embodiment. The rest of this embodiment is substantially identical with that of the first embodiment.

To evaluate the electrode surface temperature and the activation time of the multilayered gas sensing element according to this invention, a comparative multilayered gas sensing element is prepared.

Figure 17:
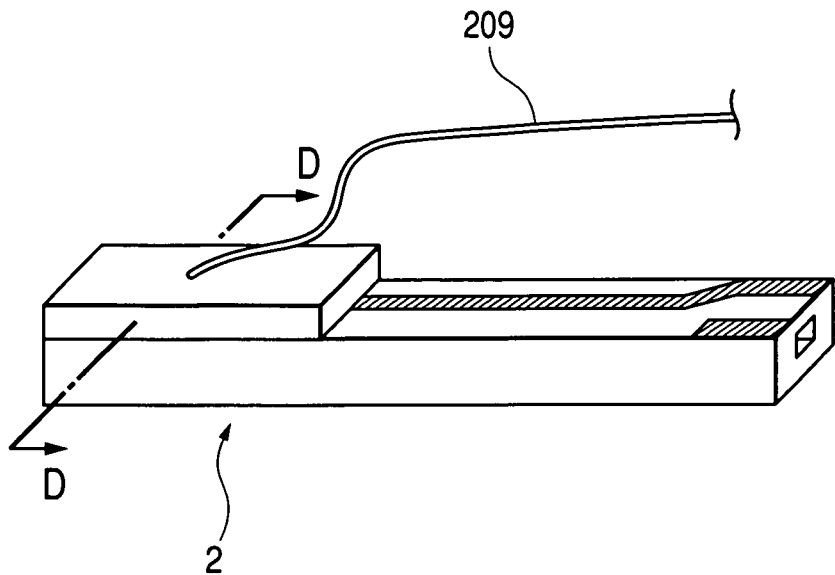
FIG. 17 is a perspective view explaining a comparative multilayered gas sensing element prepared for the comparison tests.
Figure 18:
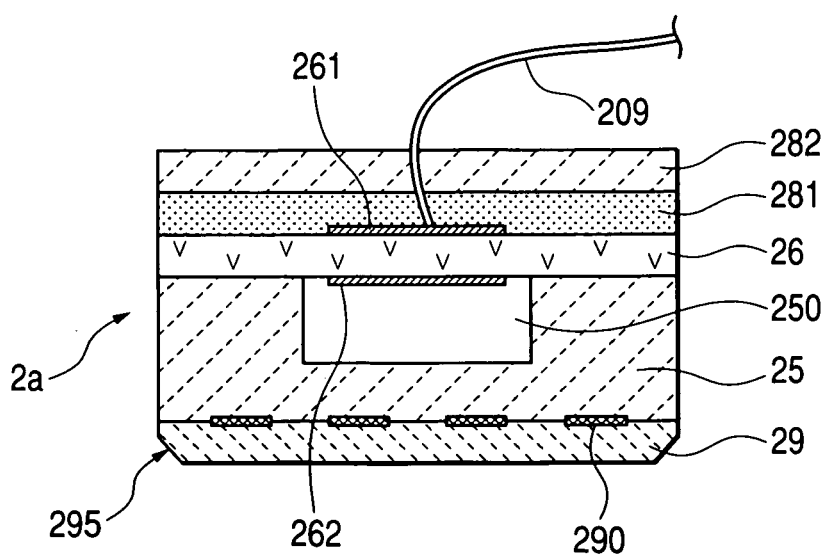
FIG. 18 is a cross-sectional view showing the comparative multilayered gas sensing element, taken along a line D—D of FIG. 17.

FIGS. 17 and 18 show the prepared comparative multilayered gas sensing element 2a, which includes a gas-impermeable protecting layer 282, a porous diffusion resistive layer 281, a solid electrolytic substrate 26, a spacer 25, and a heater substrate 29. A through hole continuously extends across the protecting layer 282 and the porous diffusion resistive layer 281 so as to reach an electrode 261. A resistance thermometer 209 equipped with a thermocouple is inserted into the through hole to measure the electrode surface temperature.

The comparative multilayered gas sensing element 2a has no wide-width portion and no narrow-width portion and therefore different, in this point, from the above-described multilayered gas sensing elements of the preferred embodiments of the present invention. The comparative multilayered gas sensing element 2a has a uniform width of 4.5 mm, as shown in FIG. 17.

Figure 20:
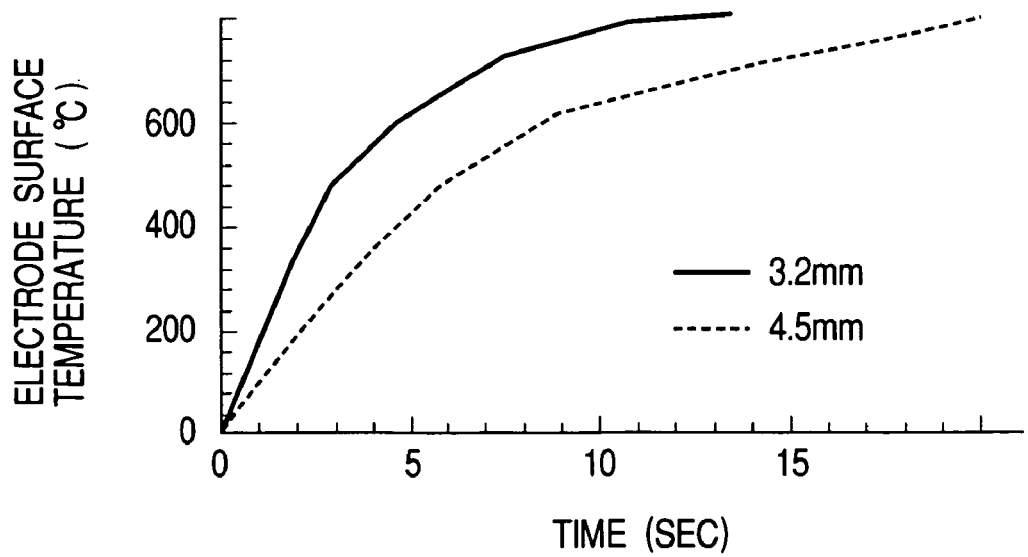
FIG. 20 is a graph showing the relationship between the electrode surface temperature and the elapsed time obtained through an evaluation test.

In the evaluation test, electric power was supplied to the heater of the multilayered gas-sensing element of the present invention and to the above comparative multilayered gas sensing element 2a. The electrode surface temperature was measured by the resistance thermometer 209. FIG. 20 shows the test result.

Meanwhile, measurement of the activation time was performed in the following manner.

First, at the room temperature of 20° C., the voltage of 0.4 V was applied between the electrode 514 (positive electrode) exposed to the reference gas chamber 532 of the sensor cell 53 and the electrode 507 (negative electrode) exposed to the measuring objective gas chamber 531 in the atmospheric environment. Next, electric power was supplied to the heat generating element 517 and the lead portion 516.

In this case, the current flowing between the electrodes of the sensor cell 53 increases with rising temperature. It is now assumed that $IL_{800}$ represents the current value at the element temperature of 800° C. The sensor can be regarded as having activated when the current value flowing between the electrodes of the sensor cell 53 has reached the level of $IL_{800} \times 0.8$. Hence, the time required for the above sensor cell current to reach the level of $IL_{800} \times 0.8$ after power supply to the heater was measured.

The relationship between the element temperature and the above sensor cell current was obtained in the following manner.

Before measuring the activation time, the heater power was adjusted with reference to the measured date of a radiation thermometer so as to stabilize the element temperature to a desired level. Then, while maintaining the sensor temperature at this level, the voltage of 0.4 V was applied between the electrode 514 (positive electrode) exposed to the reference gas chamber 532 of the sensor cell 53 and the electrode 507 (negative electrode) exposed to the measuring objective gas chamber 531 in the atmospheric environment. Under this condition, the sensor cell current was measured.

Figure 19:
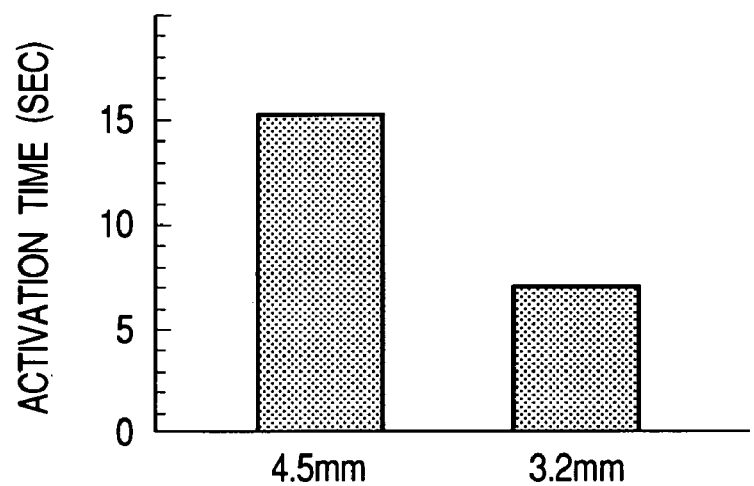
FIG. 19 is a graph showing the relationship between the width of a narrow-width portion and the activation time obtained through an evaluation test.

As shown in FIGS. 19 and 20, when the width of the narrow-width portion is 3.2 mm, the electrode surface temperature increases promptly and accordingly the required activation time is short. The difference shown in FIG. 19 is believed to derive from the fact that the heat capacity of the sensing element having the width of 3.2 mm is small compared with the comparative sensing element having the width of 4.5 mm. As apparent from the test data, the multilayered gas sensing element of the present invention having both the wide-width portion and the narrow-width portion has the capability of shortening the activation time.

Next, the relationship between the width of the narrow-width portion of the multilayered gas sensing element and the drop strength was evaluated.

For the evaluation test, various kinds of the multilayered gas sensing elements of the present invention which are identical in the wide-width portion (4.5 mm) but are differentiated in the narrow-width portion were prepared.

Figure 21:
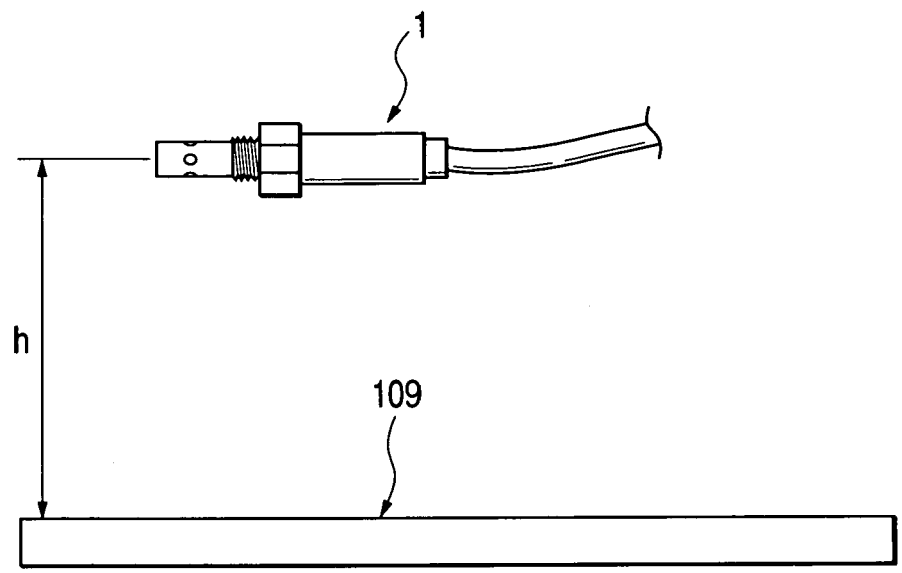
FIG. 21 is a view explaining a drop strength test.
Figure 22:
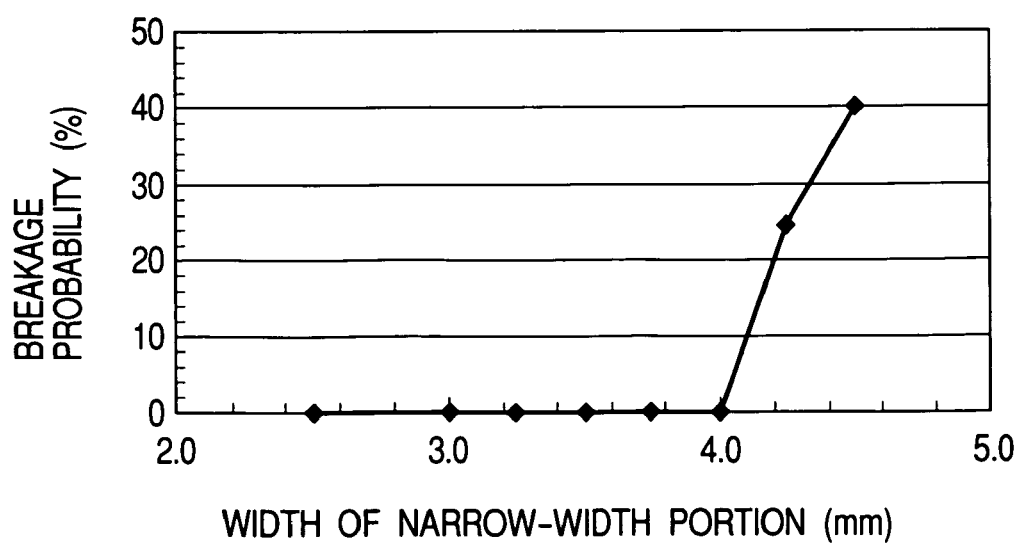
FIG. 22 is a graph showing the relationship between the width of the narrow-width portion and the breakage probability obtained through an evaluation test.

More specifically, assuming the situation that the multilayered gas sensing element is subjected to a heavy load, the gas sensor 1 was held in a horizontal position so that the longitudinal direction of the gas sensor 1 became parallel to the surface of a floor 109 as shown in FIG. 21. Next, the gas sensor 1 was dropped to the floor 109 from the height h of 1 m. FIG. 22 shows the test data representing the relationship between the breakage probability of the multilayered gas sensing element and the width of the narrow-width portion.

According to the test data of FIG. 22, the drop strength of the gas sensor can be improved and the sensing element does not crack when the width of the narrow-width portion is shorter than 4 mm.

Next, the relationship between the length of the narrow-width portion of the multilayered gas sensing element and the drop strength was evaluated.

In this evaluation test, prepared gas sensing elements of the present invention were differentiated in the longitudinal length, while the width of the wide-width portion and the narrow-width portion were fixed to 4.5 mm and 3.2 mm, respectively.

Like the above case, assuming the situation that the multilayered gas sensing element is subjected to a heavy load, the gas sensor 1 was held in a horizontal position so that the longitudinal direction of the gas sensor 1 became parallel to the surface of the floor 109 as shown in FIG. 21. Then, the gas sensor 1 was dropped to the floor 109 from the height h of 1 m.

Figure 23:
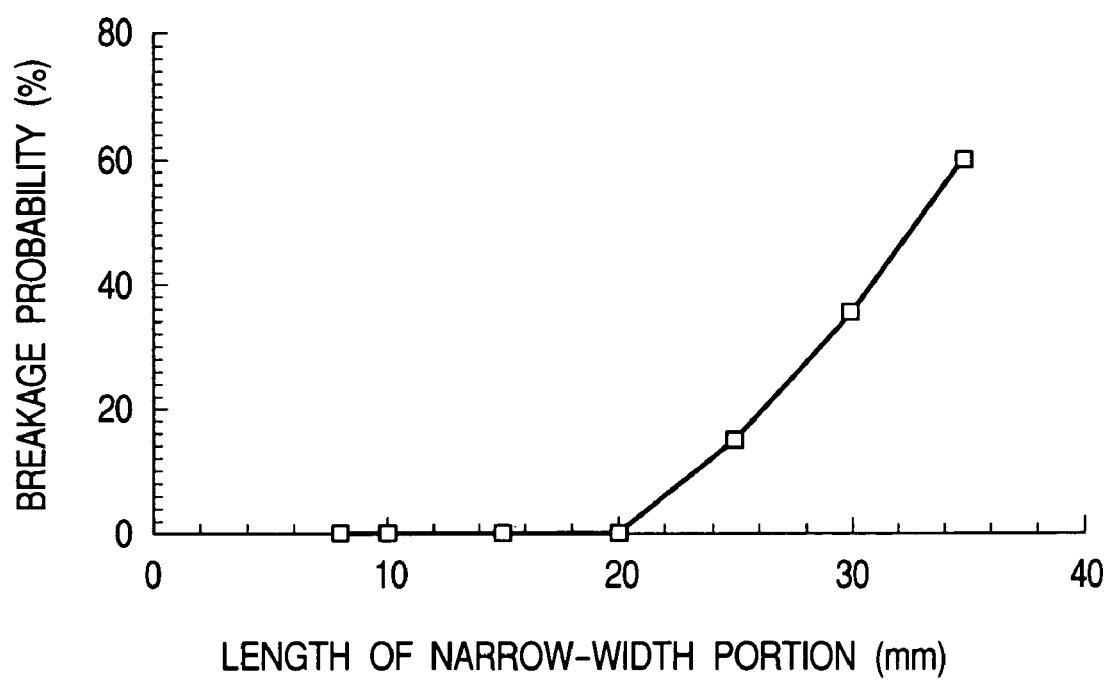
FIG. 23 is a graph showing the relationship between the length of the narrow-width portion and the breakage probability obtained through an evaluation test.

FIG. 23 shows the test data representing the relationship between the breakage probability of the multilayered gas sensing element and the length of the narrow-width portion. In this case, the length of the narrow-width portion is the length of a portion protruding from the insulator 3.

According to the test data shown in FIG. 23, the drop strength of the gas sensor can be improved and the sensing element does not crack when the length of the narrow-width portion is shorter than 20 mm.

While the invention has been shown and described in detail, the foregoing description is in all aspects illustrative and not restrictive. It is therefore understood that numerous other modifications and variations can be devised without departing from the scope of the invention.

What is claimed is:

1. A gas sensor comprising:
a cylindrical housing;
an insulator; and
a multilayered gas sensing element disposed in said housing via said insulator, said multilayered gas sensing element including a first portion, a second portion, and an intermediate portion, said first portion being in a floating relationship with respect to said insulator and having a gas sensing portion for sensing the concentration of a specific gas in a measuring objective gas, said second portion being in a fixed relationship with respect to said insulator, said intermediate portion being provided between said first and second portions, said first portion having a width less than a width of said second portion and a thickness greater than a thickness of said second portion, said intermediate portion having a width equal to the width of said second portion and a thickness equal to the thickness of said first portion.

2. The gas sensor in accordance with claim 1, wherein said multilayered gas sensing element has a corner portion being configured into a tapered or curved surface.

3. The gas sensor in accordance with claim 1, wherein said second portion has the thickness in a range from 0.7 mm to 2.0 mm and the width in a range from 4.0 mm to 6.0 mm,
said first portion has the thickness in a range from 1.3 mm to 2.4 mm and the width in a range from 2.5 mm to 4.0 mm, and
said first portion has a length equal to or larger than 8.0 mm.

4. The gas sensor in accordance with claim 1, wherein said multilayered gas sensing element comprises a sensor cell and a heater, said sensor cell comprises a solid electrolytic substrate, a first electrode provided on said solid electrolytic substrate so as to be exposed to said measuring objective gas, and a second electrode provided on said solid electrolytic substrate so as to be exposed to a reference gas, said heater comprises a heat generating element for generating heat in response to electric power supply so as to increase a temperature of said sensor cell up to an activation level; and a minimum distance between said heat generating element of said heater and a closest one of said first and second electrodes of said sensor cell is in a range from 0.4 mm to 1.8 mm.

* * * * *